United States Patent
Yodfat et al.

(10) Patent No.: US 9,457,145 B2
(45) Date of Patent: Oct. 4, 2016

(54) METHOD AND DEVICE FOR IMPROVING GLYCEMIC CONTROL

(75) Inventors: Ofer Yodfat, Modi'in (IL); Gali Shapira, Haifa (IL); Iddo M. Gescheit, Tel Aviv (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 13/574,165

(22) PCT Filed: Jan. 20, 2011

(86) PCT No.: PCT/IL2011/000061
§ 371 (c)(1),
(2), (4) Date: Oct. 16, 2012

(87) PCT Pub. No.: WO2011/089600
PCT Pub. Date: Jul. 28, 2011

(65) Prior Publication Data
US 2013/0030358 A1    Jan. 31, 2013

Related U.S. Application Data

(60) Provisional application No. 61/296,540, filed on Jan. 20, 2010.

(51) Int. Cl.
*A61M 5/172* (2006.01)
*A61B 5/145* (2006.01)
(Continued)

(52) U.S. Cl.
CPC .......... *A61M 5/172* (2013.01); *A61B 5/14532* (2013.01); *A61M 5/1413* (2013.01);
(Continued)

(58) Field of Classification Search
CPC ................ A61M 2230/201; A61M 2205/502; A61M 5/172; A61M 5/1723; A61M 5/14532
USPC .............................. 604/65, 66, 67, 503, 504
See application file for complete search history.

(56) References Cited

U.S. PATENT DOCUMENTS

2004/0077996 A1    4/2004   Jasperson et al.
2005/0192494 A1*   9/2005   Ginsberg ...................... 600/365
(Continued)

FOREIGN PATENT DOCUMENTS

WO    WO-2009066288 A1    5/2009
WO    WO-2009125398 A2    10/2009
(Continued)

OTHER PUBLICATIONS

The Diabetes Control and Complications Trial Research Group, "The Effect of Intensive Treatment of Diabetes on the Development and Progression of Long-Term Complications in Insulin-Dependent Diabetes Mellitus," N. Eng. J. Med. 1993; 329:977-986.
(Continued)

*Primary Examiner* — Theodore Stigell
*Assistant Examiner* — Benjamin Koo
(74) *Attorney, Agent, or Firm* — Dinsmore & Shohl LLP

(57) ABSTRACT

Systems, devices and methods are presented in the subject disclosure for recommending an insulin dose adapted for use with an insulin delivery device. In some embodiments, the method may include receiving blood glucose (BG) data, determining one or more insulin sensitivity (IS) values associated with the BG data, and determining an insulin dose based on the determined one or more IS values. A system for carrying out such a method is also presented.

6 Claims, 10 Drawing Sheets

(51) Int. Cl.
  *A61M 5/14* (2006.01)
  *A61M 5/142* (2006.01)
  *G06F 19/00* (2011.01)
  *A61B 5/00* (2006.01)

(52) U.S. Cl.
  CPC ....... *A61M5/14248* (2013.01); *A61M 5/1723* (2013.01); *G06F 19/3468* (2013.01); *A61B 5/4839* (2013.01); *A61M 2005/14268* (2013.01); *A61M 2205/502* (2013.01); *A61M 2205/505* (2013.01); *A61M 2205/52* (2013.01); *A61M 2230/201* (2013.01)

(56) References Cited

U.S. PATENT DOCUMENTS

| | | |
|---|---|---|
| 2005/0272640 A1 | 12/2005 | Doyle et al. |
| 2007/0106218 A1 | 5/2007 | Yodfat et al. |
| 2007/0112298 A1 | 5/2007 | Mueller et al. |
| 2007/0191702 A1 | 8/2007 | Yodfat et al. |
| 2008/0214916 A1 | 9/2008 | Yodfat et al. |
| 2008/0234663 A1* | 9/2008 | Yodfat et al. ............... 604/890.1 |
| 2008/0319381 A1 | 12/2008 | Yodfat et al. |
| 2009/0281519 A1 | 11/2009 | Rao et al. |
| 2010/0280329 A1* | 11/2010 | Randlov et al. ............... 600/300 |

FOREIGN PATENT DOCUMENTS

| | | |
|---|---|---|
| WO | WO-2009133558 A2 | 11/2009 |
| WO | WO-2011033509 A1 | 3/2011 |

OTHER PUBLICATIONS

UK Prospective Diabetes Study (UKPDS) Group, "Intensive blood-glucose control with sulphonylureas or insulin compared with conventional treatment and risk of complications in patients with type 2 diabetes (UKPDS 33)," The Lancet 1998; 353: 837-853.

UK Prospective Diabetes Study Group, "Tight blood pressure control and risk of macrovascular and microvascular complications in type 2 diabetes: UKPDS 38," BMJ 1998; 317, (7160): 703-713.

The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes," N. Engl. J. Med. 2005; 353, (25):2643-53

International Search Report and Written Opinion for International Application No. PCT/IL2011/000061, date of mailing: May 26, 2011.

* cited by examiner

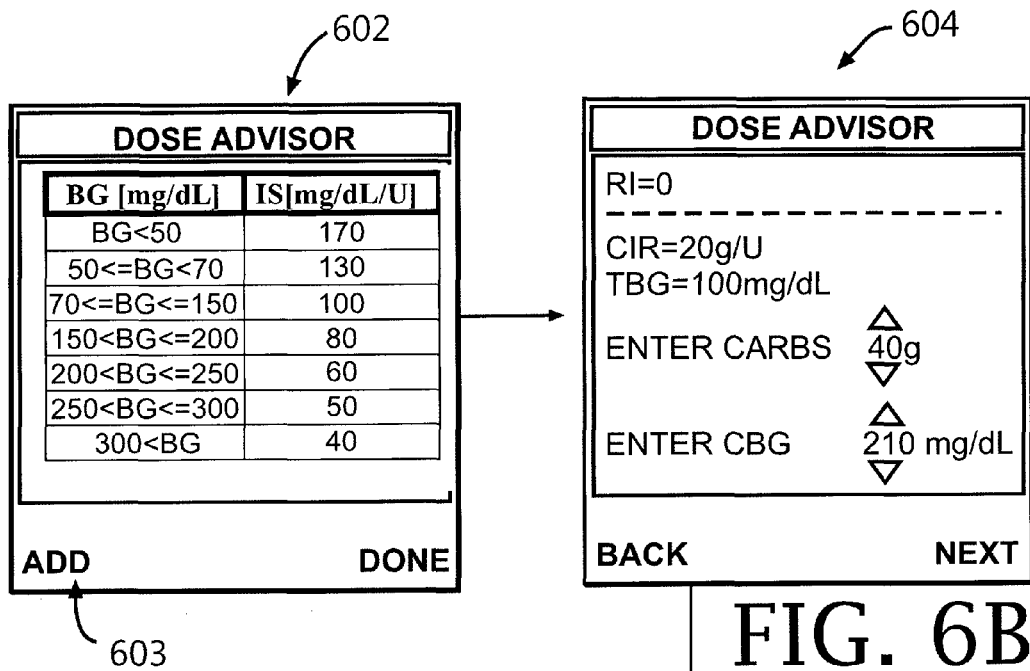
FIG. 6A
FIG. 6B
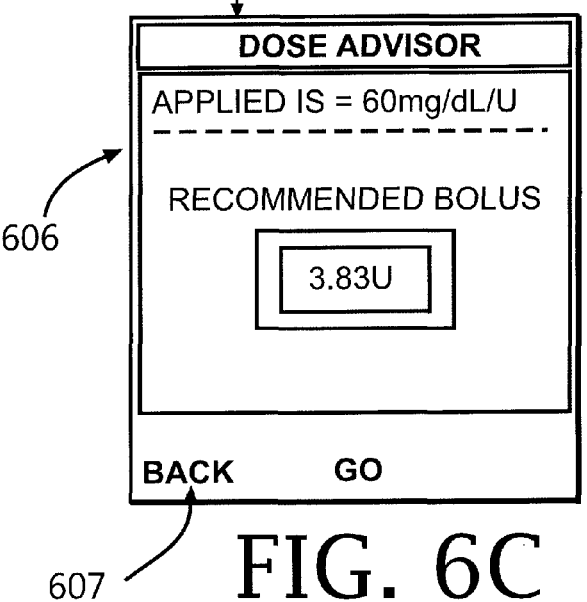
FIG. 6C

METHOD AND DEVICE FOR IMPROVING GLYCEMIC CONTROL

RELATED APPLICATIONS

This application is a national phase application of International Application No. PCT/IL2011/000061, filed Jan. 20, 2011, which claims benefit under 35 USC 119(e) of U.S. provisional patent application No. 61/296,540, filed Jan. 20, 2010. The contents of all of these applications are expressly incorporated herein by reference in their entireties.

FIELD

Methods, systems and devices for sustained medical infusion of therapeutic fluids to patients are described herein. Some embodiments relate to portable insulin infusion devices configured to monitor glucose levels of a patient as well as to methods for insulin infusion which include consideration of a patient's insulin sensitivity (IS). Some embodiments relate to methods for calculating insulin sensitivity taking into account blood glucose (BG) levels. Some embodiments relate to insulin pumps capable of adjusting insulin delivery (e.g., basal and bolus dosages) based on IS values which correspond to BG levels.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin in correspondence to blood glucose levels, maintaining near-constant glucose levels in the body.

Much of the burden of the disease to the user/patient, caregivers (e.g., physicians, Certified Diabetes Educators) and to health care resources is due to long-term tissue complications, which affect both small blood vessels (microangiopathy, causing eye, kidney and nerve damage) and large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbA1c) [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery accordingly can be of utmost importance.

Insulin pumps deliver rapid-acting insulin (e.g., Lispro, Aspart, etc.) 24 hours a day through a catheter placed under the skin. The total daily insulin dose (TDD) can be divided into basal and bolus doses. Insulin bolus doses are delivered before or after meals to counteract consumable intake such as carbohydrates loads or during periods of high blood glucose levels. The dose of the delivered bolus depends on the following parameters:

- amount of carbohydrates (Carbs) to be consumed;
- carbohydrate-to-insulin ratio (CIR)—amount of carbohydrates balanced by one unit of insulin measured in grams per one unit of insulin;
- insulin sensitivity (IS)—amount of blood glucose lowered by one unit of insulin measured in mg/dL (milligrams/deciliter) per one unit of insulin;
- current blood glucose levels (CBG), measured in mg/dL. The term "current" as in CBG relates to the BG level measured about the time of the bolus delivery (e.g., within 10 minutes prior to the bolus delivery);
- target blood glucose levels (TBG) desired blood glucose level measured in mg/dL; and
- residual insulin (RI) amount of stored active insulin remaining in the body of the patient after a recent bolus delivery (also known as bolus on board or BOB).

Conventional insulin pumps provide bolus dose recommendations that are based on the above mentioned parameters according to the following formula (hereinafter the "formula"):

$$\text{Recommended bolus} = \underbrace{(Carbs/CIR)}_{\text{"Food estimate"}} + \underbrace{(CBG - TBG)/IS}_{\text{"Correction estimate"}} - RI$$

For a non-meal related correction bolus, when the blood glucose level (BG) is out of target, the formula is simplified because carbs and optionally residual insulin can be irrelevant and thus not taken into consideration. Then, the formula can be degenerated as follows:

$$\text{Recommended bolus(correction bolus)} = (CBG - TBG)/IS.$$

The above mentioned variables may be also considered in the bolus recommendation feature described in co-owned U.S. publication no. US2008/0234663 and international patent application no. PCT/IL2009/000454 (published as WO2009/133558), the disclosures of which are incorporated herein by reference in their entireties. This bolus recommendation feature comprises sets of grids of ranges of carbohydrate and blood glucose level. Each grid corresponds to a different combination of IS, CIR, and TBG. Additional grids correspond to selected bolus doses and residual insulin values. The final recommended dose is related to a value that is substantially equivalent to the selected bolus dose minus the RI.

Basal insulin is delivered continuously over 24 hours, and maintains blood glucose levels in a specific range (e.g., between meals and overnight). Diurnal basal rates can be pre-programmed or manually changed according to various daily activities (e.g., walking, sleeping, and sport activity), illness and the like. The basal insulin rate/dose may also depend on the user's IS value.

It is apparent to one skilled in the art that accurate IS values are critical for maintaining euglycemia for diabetic patients. IS can be essential in determination of the administered basal dose and the administered bolus dose, especially that of the correction bolus dose.

Typically, the majority of type 1 diabetes patients use a single IS value, assuming that IS has a constant value (i.e., does not change over time) which is independent and does not change upon other occurrences and/or factors.

Alternatively, different IS values are used in different time slots of the day. For example, pump users may set a greater IS value in the evening hours after daily exercise since the sensitivity to insulin increases when physically active.

SUMMARY

Systems and devices for adjusting and delivering insulin and methods for determination of the delivered bolus and/or basal dosages are provided in the present disclosure (hereinafter "dose advisor", or "dose advisor application"). In some embodiments, the insulin dosage is based on an IS value that depends on the user's BG level (or any other body glucose level which corresponds to the BG, such as glucose level measured in the interstitial fluid (ISF)). The BG level may be provided by at least one of: a continuous glucose monitor (CGM), consecutive or periodic blood glucose measurements (e.g., via a glucometer), or any other means for measuring body glucose levels.

In some embodiments, a BG level or a range of BG levels can be correlated or assigned to a corresponding IS value. For example, the following BG ranges may be assigned the following IS values:

BG<50→*IS=170mg/dL/U
50≤BG<70→*IS=130mg/dL/U
70≤BG≤150→IS=100mg/dL/U
150≤BG≤200→IS=80mg/dL/U
200<BG≤250→IS=60mg/dL/U
250<BG≤300→IS=50mg/dL/U
300<BG→IS=40mg/dL/U

In some embodiments, the correlation (e.g., mathematical relation, empirical relation) follows a general behavior in which the greater the BG level, the lower the IS value.

In some embodiments, the insulin dosage is based on an IS value that depends on the trend (e.g., fall, rise) and rate of change of BG level (hereinafter "BG trend"). The BG trend may be provided by a continuous glucose monitor (CGM), consecutive blood glucose measurements, or any other means for acquiring body glucose levels.

In some embodiments, a combination of BG level or range of BG levels and BG trend can be assigned, correlated or otherwise matched to an IS value or IS range. For example, a high BG level which is relatively constant over time (i.e., constant trend) can be assigned to a relatively low IS value while a high BG level which is rapidly decreasing (i.e., rapid falling trend) can be assigned to a greater IS value. Similarly, a low BG level that is relatively constant can be assigned to a high IS value but if the BG level is also increasing rapidly, a lower IS value would be assigned.

In some embodiments, one or more IS values can be assigned or otherwise matched to one or more time slots of the day, to correspond to varying BG levels or recognized BG level patterns over the day.

In some embodiments, BG level and trends may imply not only an IS value, but also an IS trend, e.g., in correspondence to BG behavior and/or prediction, the IS may vary. This may affect on the administered dosage (bolus and/or basal).

For example, according to some embodiments, a BG level of 280 mg/dL would be assigned an IS value of 50 mg/dL/U according to the above example. However, if the BG is decreasing rapidly at a rate of 2 mg/dL/min, then in 30 minutes, the BG is expected to be 220 mg/dL and an IS of 60 mg/dL/U is appropriate for calculation of a bolus dose (for example). On the other hand, a BG level of 60 mg/dL would be assigned an IS value of 130 mg/dL/U according to the above example. However, if the BG is increasing rapidly at a rate of 2 mg/dL/min, then in 30 minutes, the BG is expected to be 120 mg/dL and an IS of 100 mg/dL/U is appropriate for calculation of a bolus dose (for example).

Accordingly, for these embodiments, recommendation of a bolus dose may be based on the formula according to BG dependent IS value.

For example, in the above example, a BG level of 120 mg/dL is assigned an IS value of 100 mg/dL/U. If the user's target BG (TBG) is 100 mg/dL, CIR is 20 g/U, the amount of carbohydrates (Carbs) consumed is 40 g, and there is no residual insulin (RI), then the recommended bolus may be calculated as follows:

Recommended bolus=(Carbs/CIR)+(CBG−TBG)/IS−
RI=40/20+(120−100)/100−0=2.2U

Alternatively, each IS value can be assigned to a certain multiplier value (MV) and the bolus dose can be calculated based on a normoglycemic IS (NIS) and then multiplied by the relevant (or corresponding) MV.

If, for example, the aforementioned formula is used, the bolus recommendation may be calculated as follows:

Recommended bolus=[(Carbs/CIR)+(CBG−TBG)/
NIS]×MV−RI

For example, the following MVs may be assigned to the following IS values (presented as a fraction of NIS):
0.5NIS<IS<0.7NIS→MV=1.7
0.7NIS<IS<0.9NIS→MV=1.5
0.9NIS<IS<1.1NIS→MV=1
1.1NIS<IS<1.3NIS→MV=0.8
1.3NIS<IS<1.6NIS→MV=0.6
1.6NIS<IS<2NIS→MV=0.5

Thus, if (for example) the user's NIS is 100 mg/dL/U, the target BG is 100 mg/dL, the current BG is 220 mg/dL, CIR is 20 g/U, the amount of carbohydrates consumed is 40 g, and there is no residual insulin (RI), then the recommended bolus can be calculated as follows:

Recommended bolus=(Carbs/CIR)+(CBG−TBG)/IS−
RI=40/20+(120−100)/100−0=2.2U

However, if the IS value assigned to CBG of 220 mg/dL is 60 mg/dL/U which is 0.6 NIS, the MV is therefore 1.7 and the recommended bolus is 3.74 (i.e., 2.2×1.7).

Alternatively, the bolus recommendation may be calculated using an alternative MV, as the following:

Recommended bolus=[(Carbs/CIR)+(CBG−TBG)/
(NIS×MV)]−RI

If, for example, the MVs assigned to the different BG levels is as follows:
BG<50→MV=0.6
50≤BG<70→MV=0.8
70≤BG≤150→MV=1
150<BG≤200→MV=1.2
200<BG≤250→MV=1.4
250<BG≤300→MV=1.5
300<BG→IS=MV=1.6

Then, the recommended bolus for the above example would be:

Recommended bolus=40/20+(220−120)/(100*1.4)−
0=2.7U where MV is the multiplier value Generally, according to some embodiments, when the BG dependent IS is less than the NIS, the MV would be greater than 1. If the BG dependent IS is greater than NIS, the MV would be smaller than 1.

Alternatively, in some embodiments, each IS value or BG range is assigned to an absolute value of insulin dose ("AI") which is then added or subtracted from a bolus dose based on a normoglycemic IS. Generally:

when the IS is less than the normoglycemic IS, the AI is added to the intended bolus dose (as more insulin required), and when the IS is greater than the normoglycemic IS, the AI is subtracted from the intended bolus dose (less insulin required).

Accordingly, the bolus recommendation may be calculated as the following:

$$\text{Recommended bolus} = [(\text{Carbs}/\text{CIR}) + (\text{CBG} - \text{TBG})/\text{NIS} - \text{RI} + \text{AI}]$$

For example, if the AIs are assigned to the different BG levels as follows:

BG<50→AI=−1U
50≤BG<70→AI=−0.8U
70≤BG≤150→AI=0U
150<BG≤200→AI=0.4U
200<BG≤250→AI=0.6U
250<BG≤300→AI=0.8U
300<BG→IS=AI=1U

Accordingly, the recommended bolus for Carbs=40 g, CIR=20 g/U, CBG=220 mg/dL, TBG=100 mg/dL, RI=0, and NIS=100 mg/dL/U, is:

$$\text{Recommended bolus} = 40/20 + (220-120)/100 - 0 + 0.6 = 3.6U$$

According to some embodiments, the basal rate is also multiplied by the relevant MV, so it is increased or decreased by a certain percentage if a high or low BG level is measured, respectively.

Numerical example:
Basal rate programmed at 1 U/h
Normoglycemic IS=80 mg/dL/U
Measured BG level=40 mg/dL
IS when BG level is in the range of 30 to 50 mg/dL=120 mg/dL/U
MV assigned to IS of 120 mg/dL/U=0.7

Thus, the basal rate is decreased to 0.7 U/h (i.e., 1 U/h*0.7).

In some embodiments, basal rate may be adjusted dependent on the BG level characteristics. For example, discrete measurements of BG levels (e.g., via a glucometer) may render periodic adjustment of the IS value. Alternatively, continuous measurements of BG levels (e.g., via a CGM) may render continuous or periodic (with high frequency) adjustment of the IS value(s).

In some embodiments, the IS value(s) may be related to other patient variables such as health related parameters (e.g., body temperature, heart rate), activity level (e.g., sport activity, sleeping, walking), illness, and the like.

In some embodiments, the user and/or caregiver can assign (or otherwise match) different IS values to different BG levels and/or BG trends when initially setting the insulin pump. In further embodiments, the user and/or caregiver can assign different MVs and/or absolute insulin doses (AIs) to IS values when initially setting the insulin pump.

In some embodiments, the fluid delivery device includes a remotely controlled dispensing unit that can be comprised of a reusable part and a disposable part. The disposable part contains a reservoir, outlet port and other relatively inexpensive components. The reusable part contains electronics (e.g., PCB, processor), at least a portion of driving mechanism (pump), and other relatively expensive components (e.g., sensors). In some embodiments, operation of the fluid delivery device is carried out manually by operating buttons/switches located on the dispensing unit. In some embodiments, the fluid delivery device further comprises a cradle that adheres to the skin and allows disconnection and reconnection of the dispensing unit from and to the patient's skin, upon patient discretion. The cradle can be coupled to subcutaneously insertable cannula enabling insulin delivery into the subcutaneous compartment of the patient.

In some embodiments, the device can be coupled to a CGM and comprise a memory that stores BG data (e.g., measured BG levels), and a processor for controlling the continuous BG measurements and providing the BG trends.

In some embodiments, a drug delivery device is provided and includes a pump for dispensing the drug into a body of a user, input means for receiving at least one of blood glucose (BG) data and one or more insulin sensitivity (IS) values, a processor having a dose advisor application operating thereon configured to determine the one or more IS values based on the BG data, a memory for storing the BG data and the one or more IS values, and a display for presenting output associated with the one or more IS values.

In some embodiments, a method for recommending an insulin dose adapted for use with an insulin delivery device is provided and includes receiving blood glucose (BG) data, determining one or more insulin sensitivity (IS) values associated with the BG data, and determining an insulin dose based on the determined one or more IS values.

Still, other embodiments may further include any one or more of the following additional features (steps, data, and/or structure):

the BG data comprising BG level and optionally BG trend;

receiving BG data includes at least one of receiving an input from a user, and receiving a signal from a glucose monitor;

determining the one or more IS values includes at least one of selecting the one or more IS values from a table, calculating the one or more IS values, modeling or correlating the one or more IS values with respect to empirical data, and matching the one or more IS values to BG data— determining establishes a relationship between the one or more IS values and the BG data;

visually presenting the one or more IS values as a function of BG data;

visually presenting includes presenting a graph or a table showing matching between the one or more IS values and the BG data;

visually presenting the one or more IS values in a form of a range;

retrieving from a memory the one or more IS values associated with BG data;

the insulin dose including at least one of a bolus component and a basal component;

delivering the insulin dose a body of a user; and providing an insulin pump having a processor having a dose advisor application operating thereon, the dose advisor being configured to determine the one or more IS values and the insulin dose, and initiating delivery of the insulin.

BRIEF DESCRIPTION OF THE DRAWINGS

FIGS. 6a-c illustrate exemplary user interface for the dose advisor according to some embodiments.

DETAILED DESCRIPTION

Figure 1:
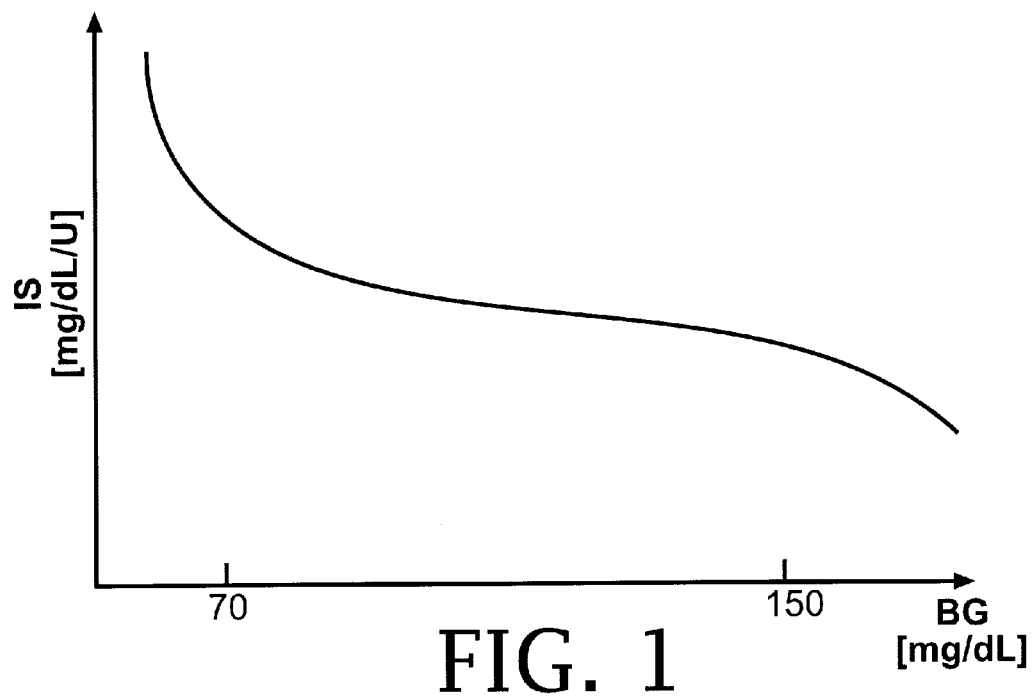
FIG. 1 is a graphical representation of IS values as a function of BG levels.

FIG. 1 is a graphical representation of IS values as a function of BG levels. IS values rise and fall when BG is relatively low (e.g., BG<70 mg/dL) or relatively high (e.g., BG>150 mg/dL) respectively. In the relatively normoglycemic range (e.g., 70 mg/dL<BG<150 mg/dL), IS values are substantially constant. The low insulin sensitivity in the hyperglycemic range may be, in some instances, due to a phenomenon known as glucose toxicity.

Figure 2A:
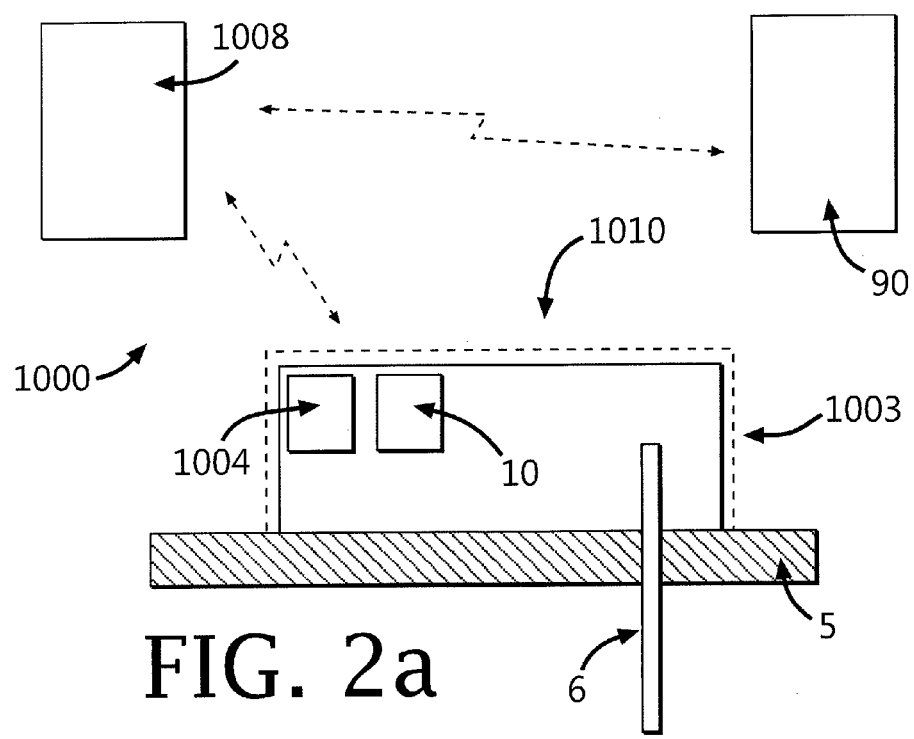
FIGS. 2a-c illustrate a fluid delivery device including an insulin dispensing unit and a remote control unit according to some embodiments. The dose advisor application may be resident on a processor, or stored in a memory for operation on a processor; the processor may be located in the remote control unit and/or in the dispensing unit.
Figure 2B:
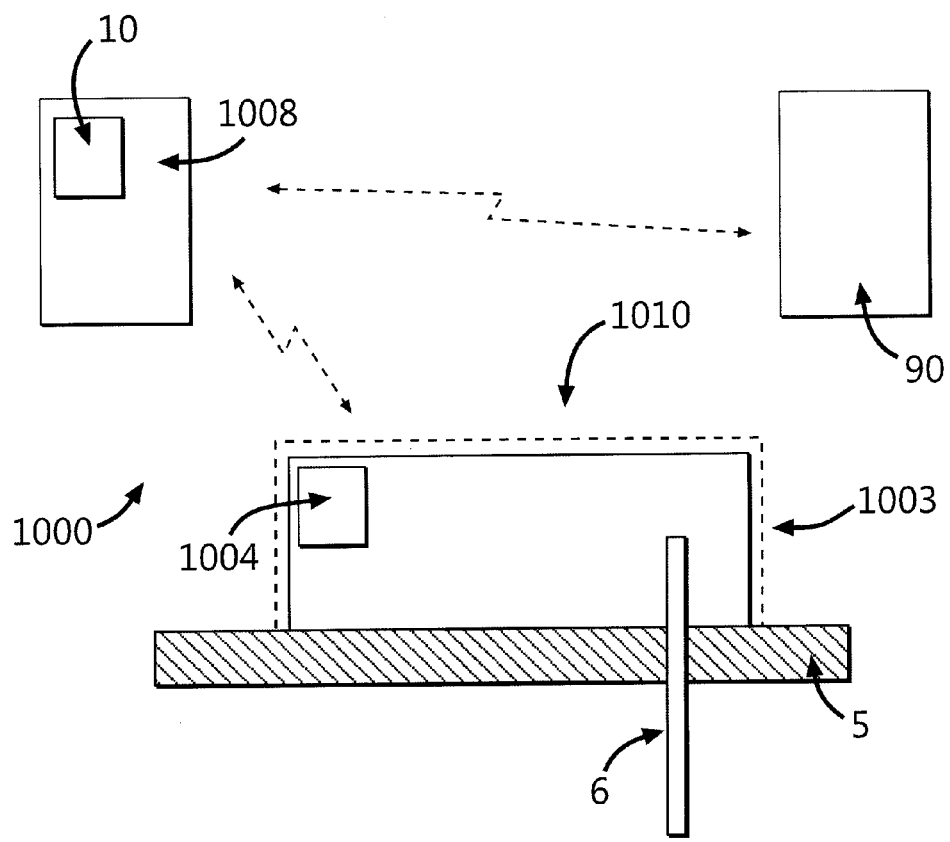
Figure 2C:
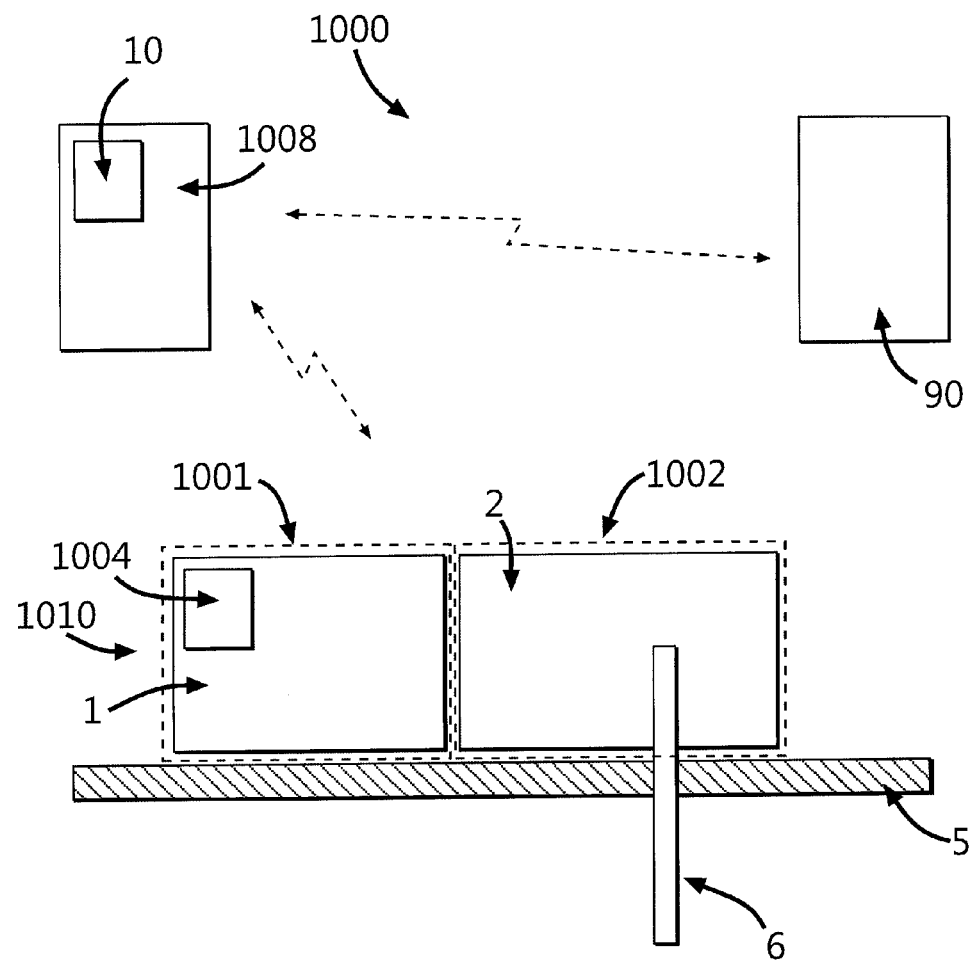

FIGS. 2a-c illustrate an exemplary device/system 1000, according to some embodiments, for dispensing insulin to the body of a patient/user. The device comprises a dispensing unit 1010 that includes a pump (e.g., syringe-piston, peristaltic), and may also include at least one or more of the following: a remote control unit 1008, and a blood glucose (BG) monitor 90. The dispensing unit 1010 may be coupled to a cannula 6 that penetrates the user's skin 5 to deliver insulin to the subcutaneous tissue. In some embodiments, the dispensing unit 1010 can be comprised of a single part having a single housing 1003 (as shown in FIGS. 2a-b) or two parts having two housings 1001, 1002 (as shown in FIG. 2c). In some embodiments, a first part 1 can be reusable (also referred-to as "reusable part") and a second part 2 can be disposable (also referred-to as "disposable part").

Flow programming and data acquisition can be done by the remote control unit 1008 or by one or more operating buttons/switches 1004 located on the dispensing unit's housing. The device 1000 may include at least one processor, at least one memory, at least one input means (e.g., keypad, buttons, switches, touch-screen, voice commander, etc.), at least one screen, and at least one notification means such as audible (e.g., buzzer) and/or vibration (e.g., vibrator) to notify the user. Each of these features can reside in at least one of: the remote control unit 1008, the dispensing unit 1010. In some embodiments, the remote control unit may be implemented in a Personal Data Assistance (PDA), a cellular phone, a watch, a media player (e.g., iPod), a smart-phone, a laptop and/or the like. The device can further include at least one of a blood glucose monitor (BGM) and a continuous glucose monitor (CGM). The BGM and/or CGM can be contained within the remote control unit and/or the dispensing unit or be a separate unit being capable to communicate (either one- or two-way communication) with the dispensing unit and/or the remote control unit.

Such a device/system is disclosed in co-owned U.S. publication no. US2007/106218 and in co-owned international application no. PCT/IL09/000,388 (published as WO2009/125398), the disclosures of which are herein disclosed by reference in their entireties.

In some embodiments, the dose advisor can be resident (e.g., operating) on a processor 10 which can be located in the dispensing unit 1010 (see FIG. 2a), in the remote control unit 1008 (see FIGS. 2b-c) or be shared between the two units (1010 and 1008). In such embodiments, the dose advisor is capable of recommending a bolus and/or basal dose in accordance with a BG-dependent IS.

Figure 3A:
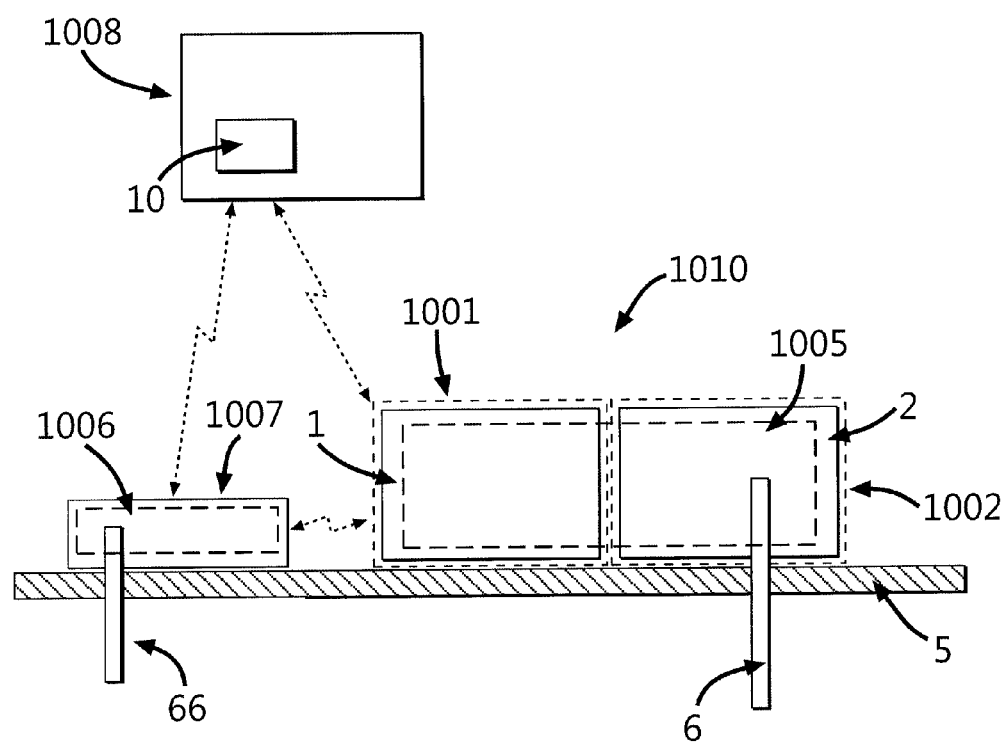
FIGS. 3a-b illustrate a fluid delivery system that includes remotely controlled continuous dispensing apparatus and sensing apparatus according to some embodiments. The sensing apparatus can be either separated from the dispensing apparatus (see FIG. 3a) or integrated therewith (see FIG. 3b).
Figure 3B:
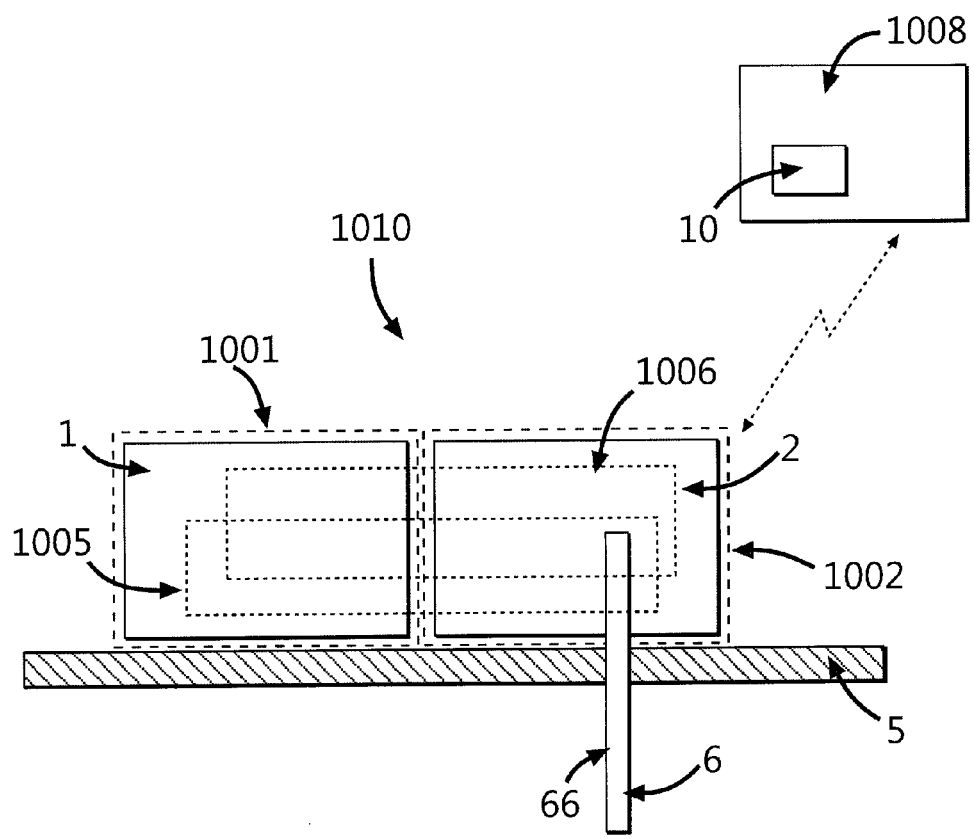

FIGS. 3a-b illustrate a device/system that comprises a two-part insulin dispensing unit 1010, a remote control unit 1008 and a continuous glucose monitor (CGM) unit 1007. The two-part dispensing unit may comprise a reusable part 1 and a disposable part 2. A dispensing mechanism 1005 may be shared between the reusable and disposable parts.

In some embodiments, the dose advisor can be included within the remote control unit 1008, as illustrated in FIGS. 3a-b, or within the dispensing unit 1010, for example.

FIG. 3a illustrates a system, according to some embodiments, that comprises a separate dispensing unit 1010 and a separate CGM unit 1007. The CGM unit 1007 may include at least one of a probe 66, and a sensing mechanism 1006 (also referred-to as "sensor"), where the mechanism may comprise a processor, a transmitter or transceiver, and a memory. Continuous glucose readings may then be transmitted to the remote control unit 1008 and therefrom to the dispensing unit 1010 (indicated by the dashed arrows). In some embodiments, communication can be established directly between the CGM unit 1007 and the dispensing unit 1010 (indicated by the dashed arrows).

FIG. 3b illustrates a system that comprises a two-part integrated unit 1010 that includes both the dispensing mechanism 1005 and the sensing mechanism 1006. In some embodiments, the cannula 6 can include the probe 66, as described, for example, in co-owned U.S. application Ser. No. 11/706,606 (published as US2007/0191702) and U.S. application Ser. No. 11/963,481 (published as US2008/0214916), and International Patent Application No. PCT/IL08/001,521 (published as WO2009/066288), the contents of all of which are hereby incorporated by reference in their entireties. In some embodiments, the cannula 6 and probe 66 may reside apart so that insulin is delivered in one site and glucose is sensed in another site.

In some embodiments, insulin can be automatically dispensed by the dispensing mechanism 1005 according to continuous BG level readings generated by the sensing mechanism 1006 (e.g., a closed loop mode). In other embodiments, basal delivery can be automatically modified according to continuous BG level readings and boluses can be manually administered by the user (e.g., open loop mode or semi-open loop mode) using the dose advisor recommendations (for example).

Figure 4:
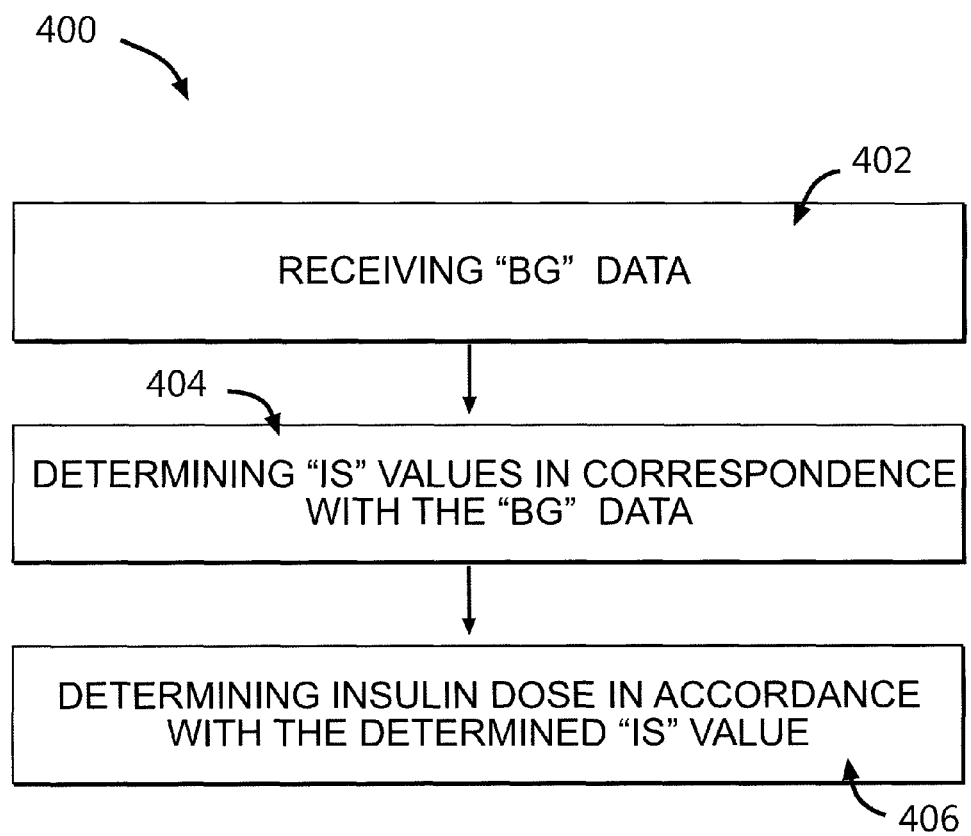
FIG. 4 is a block diagram of a method for determining an insulin dose based on an IS value according to some embodiments, with the IS value being determined based on the BG level.

FIG. 4 is a block diagram of a method 400, according to some embodiments, for determining an insulin regime, e.g., bolus and/or basal dosages. In some embodiments, the method 400 comprises receiving 402 BG data. The BG data can include body glucose concentration levels, such as blood glucose levels or glucose measured in ISF. The BG levels may include discrete values (e.g., 180 mg/dL), numerical ranges (e.g., 175 mg/dL-185 mg/dL) or other forms of presentations such as "HIGH" level, representing for example a predefined range which can be configured by the user. The BG data can further include the trend of change of BG levels (e.g., rising or falling concentration, the rate of change), and the time (and in some embodiments, the time and date) of the measurement. In some embodiments, the BG data can be acquired by one or more of a glucometer, a CGM, an integrated blood glucose meter (IBGM) or by any other means for measuring body glucose levels. In some embodiments, receiving the BG data can include one of: measuring BG levels, receiving BG data from a remote location such as via wireless communication (e.g., from a remote glucometer) or receiving a corresponding signal from a processor of a CGM, and retrieving the BG data from a memory, for example.

The method 400 further comprises determining 404 an IS value in correspondence with the BG data. In some embodiments, determining the IS value can include one of: selecting the IS value from a table/schedule in which IS values corresponds to BG levels, calculating, modeling and/or correlating the IS values via mathematical formula or analytical and/or empirical correlation which matches an IS value to BG level.

In some embodiments, the relation between IS values and BG values may be represented as illustrated in FIG. 1. In some embodiments, the relation between BG levels and IS values can be one of: predefined (e.g., by the user, caregiver or pump manufacturer), adapted (or "tailored") for each user (either manually or automatically), or customized at user's discretion.

Then, an insulin dosage or regime (e.g., bolus and/or basal dosages) can be determined 406 in accordance with the determined IS value. In some embodiments, determining 406 the insulin dose can include bolus dose calculations according to the formula, basal dose calculations, or implementing processing techniques such as neural networks, fuzzy logic, logistic regression, random forest, etc. An example for calculating a basal dose using the IS value and multiplier values (MVs) is disclosed in co-owned International Patent Application No. PCT/IL2010/000757, claiming priority to U.S. Provisional Application No. 61/243,860, the disclosures of which are hereby incorporated by reference in their entireties. In some embodiments, additional factors may be taken into consideration in determining the IS value, including, without limitation, activity level, presence of an illness, body temperature, level of emotional stress, heart rate, ventilation rate, insulin absorption rate, administration site, etc.

In some embodiments, the method 400 can further include administering the bolus dose accordingly. In some embodiments, the method 400 can further include receiving inputs (e.g., confirmations, rejections, physical activity, and amount of carbohydrates) from a user and/or notifying the user, for example displaying data on a screen. In some embodiments, the method 400 further includes storing IS values in a memory. The IS value can be discrete and constant to be used during a period of time (e.g., daily, weekly, yearly). In other embodiments, an IS value may be set to numerous diurnal periods of time (e.g., $IS_1$ for 08:00-12:00, $IS_2$ for 12:00-17:00, $IS_3$ for 17:00-22:00, etc.). In some embodiments, IS values may change continuously or periodically over time. Then, if BG levels are continuously or periodically monitored via a CGM, the IS value can be continuously or periodically adjusted accordingly.

In some embodiments, the method 400 can be implemented in an insulin pump and be operated by a dose advisor. The dose advisor may be an application program which may operate on or in conjunction with a processor 10 to carry out the control and calculations, and/or in conjunction with a memory to store the data (e.g., BG levels and IS levels) and/or in conjunction with a transceiver to receive and/or transmit data from and to a glucose sensor, insulin pump, and/or the like. In further embodiments, the dose advisor is further capable of processing and analyzing the data to control and improve insulin delivery. For example, it may be capable of executing analytical and/or statistical analyses over the data to derive a curve fit approximation for the relationship between the IS and BG values. The dose advisor may further receive data and/or instructions via input means (e.g., buttons, switches, keypad, touch-screen, voice commander) and/or notify the user via output means such as visual (e.g., screen), audible (e.g., buzzer), tactile (e.g., vibrator) notifications. Accordingly, delivering the insulin dosages can be performed by the insulin pump.

Figure 5:
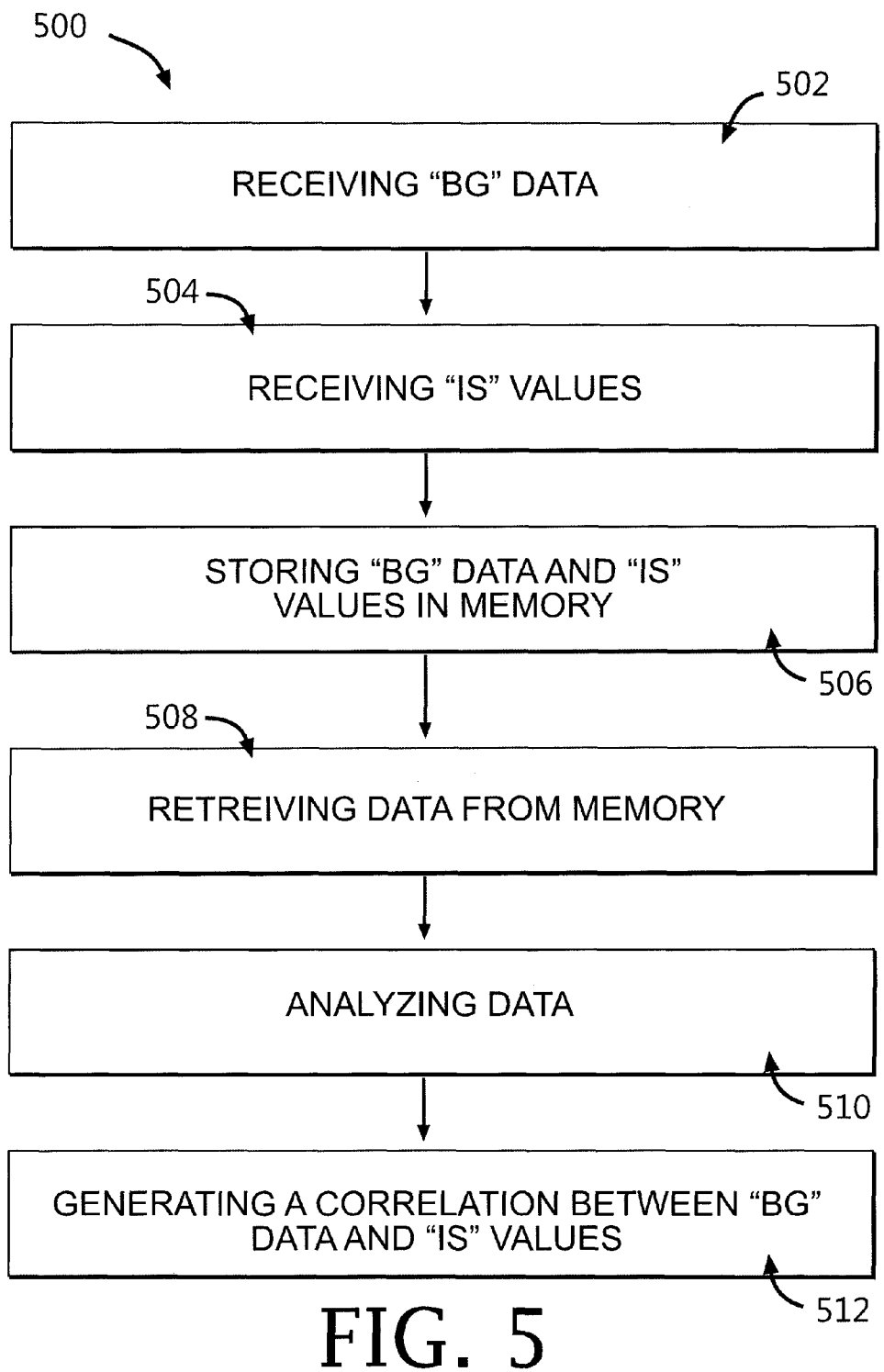
FIG. 5 is a block diagram of a method for creating a correlation between a user's BG data and IS values according to some embodiments.

FIG. 5 is a block diagram of a method 500 according to some embodiments of the present disclosure, for creating a correlation, relation or otherwise match between a user's BG data and IS values. For example, after collecting the data, i.e., receiving 502 the BG data and receiving 504 the IS values, the collected data can be stored 506 in a memory. The memory can be located in an insulin pump (e.g., in the dispensing unit and/or remote control) and/or in an external device such as PC, laptop, media player, smart-phone, or web-based database. The collection of data may be performed along a period of time (e.g., a week, a month, 6 months). Then, when needed (e.g., at the discretion of the user or caregiver), the data can be retrieved 508 from the memory. Analyzing 510 the data enables generation 512 of a correlation (e.g., relation, match) between BG data and IS values. This correlation can be stored in a memory and be presented to the user. Analyzing 510 the data may comprise mathematical and statistical operations such as one or more of curve fitting, smoothing, interpolating, classifying, clustering, and/or the like. It can be done, for example, by employing analytical tools and/or machine-learning algorithms (e.g., regressions, neural networks, fuzzy logic, etc.). In some embodiments, setting the IS value in an insulin pump can be based on this correlation, given BG data (e.g., BG level of a user). In further embodiments, the data and/or its analyses can be presented to the user over a screen, for example.

FIGS. 6a-c illustrate an exemplary user interface associated with the dose advisor according to some embodiments. For example, FIG. 6a illustrates a window 602 displaying an example of the correlation between BG levels and IS values in a form of a table. Alternatively, the correlation can be achieved via mathematical correlation or calculation. As shown in FIG. 6a, the user may customize the table by using the "Add" option 603. In other embodiments, customization of this data may be restricted.

FIG. 6b illustrates a window 604 employed by the dose advisor for determining a bolus dose. This window 604 may be used to display relevant parameters such as CIR and TBG. In some embodiments, the window 604 may be also used to receive parameters, for example, the user can input the amount of carbohydrates (Carbs) he/she is about to consume or the level of BG (also referred-to as "CBG"). The determination of bolus dose is carried out based on an IS value which corresponds with the correlation presented in FIG. 6a, for example.

FIG. 6c illustrates an example of a window 606 which displays the IS value used for the bolus dose determination (i.e., "Applied IS") and the determined bolus dose ("Recommended Bolus"). In some embodiments, the user may accept this recommendation and instruct the pump to administer it, for example by using the "Go" option 607. In other embodiments, the user may reject the recommendation and input different value for the bolus dose.

Figure 7:
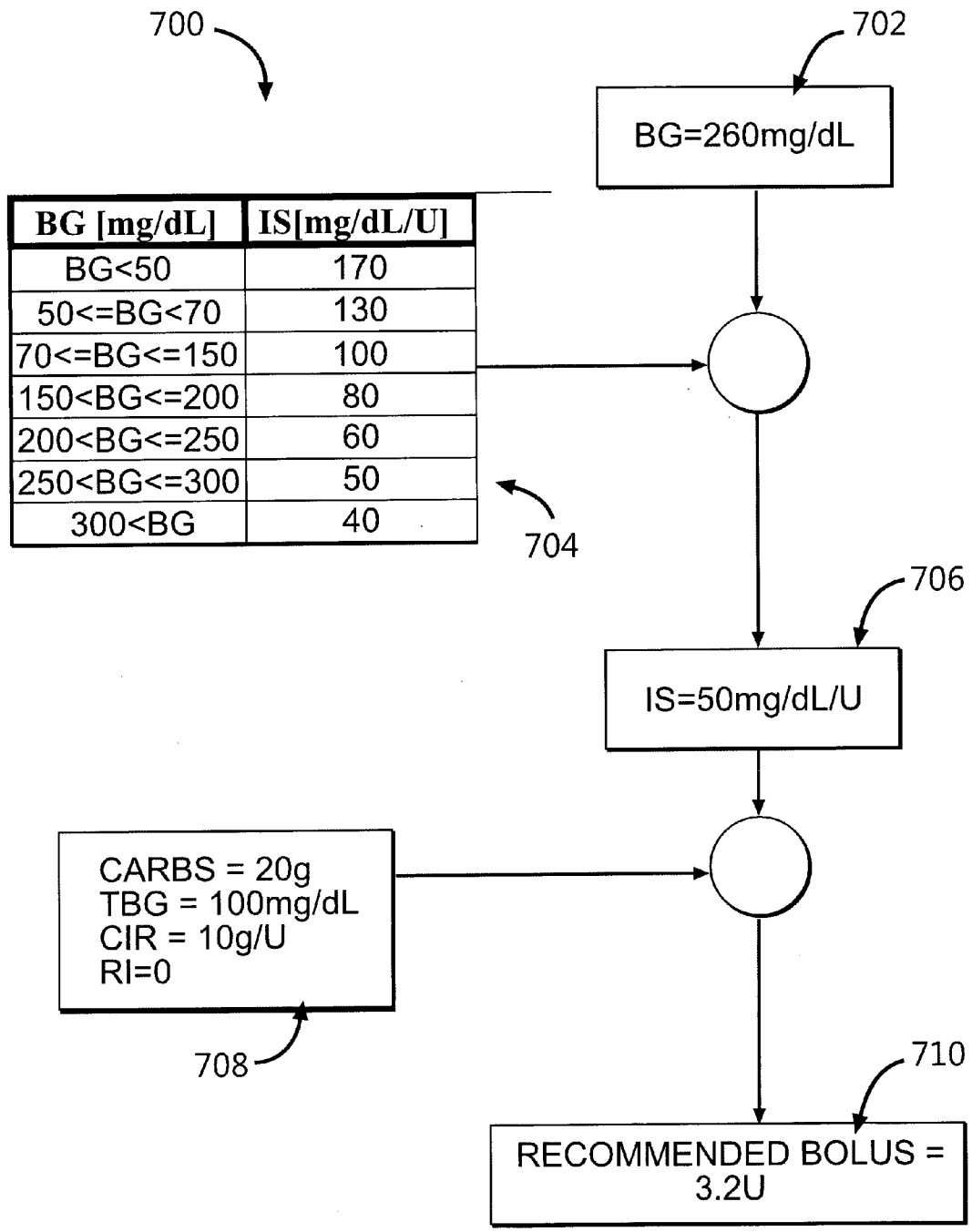
FIG. 7 shows a numerical example for determining an insulin bolus dose according to some embodiments.

FIG. 7 is a numerical implementation 700 of the method depicted in FIG. 4 for determining a bolus dosage, according to some embodiments. For example, after a BG value (e.g., 260 mg/dL) is received 702, measured via a glucometer (for example) and inputted by the user, the dose advisor determines 706 an IS value (e.g., 50 mg/dL/U) in accordance with the table 704 stored in the memory. Then, the dose advisor can take into account 708 other parameters (some of which may be inputted by the user, received from a remote source, etc., which may be being stored in the memory) and determine 710 the recommended bolus, for example, via employing the formula Recommended Bolus=(Carbs/CIR)+(CBG−TBG)/IS−RI, i.e., in this example Recommended Bolus=(20/10)+(260−100)/50−0=3.2 U.

Figure 8:
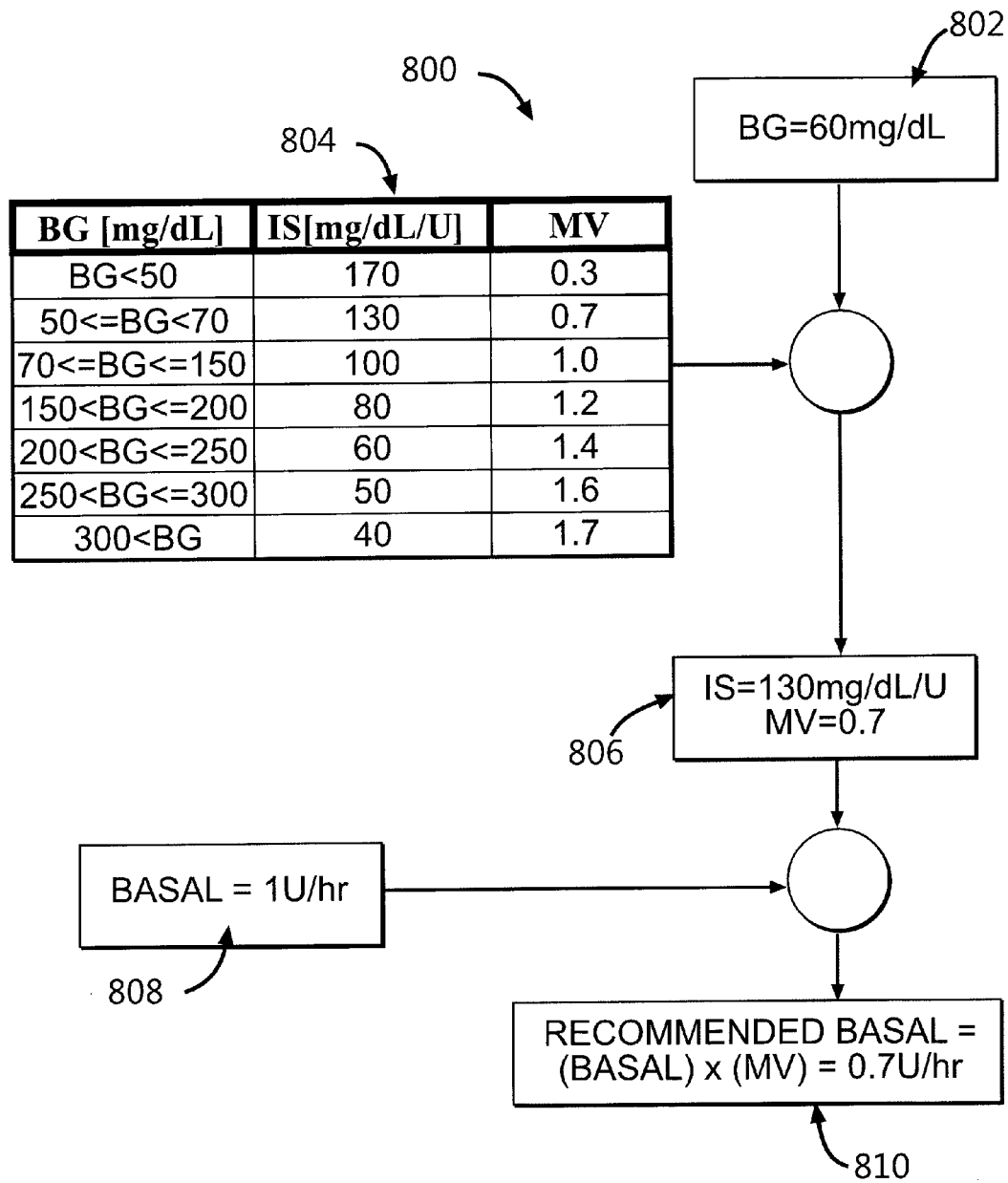
FIG. 8 shows a numerical example for determining an insulin basal dose according to some embodiments.

FIG. 8 is a numerical implementation 800 of the method depicted in FIG. 4 for determining a basal dosage (i.e., basal rate), according to some embodiments. After a BG value (e.g., 60 mg/dL) is received 802, the dose advisor determines 806 an IS value (e.g., 130 mg/dL/U) and MV value (e.g., 0.7), in accordance with the table 804 stored in the memory. Then, the dose advisor can take into account 808 other parameters (e.g., the current basal rate of 1 U/hr) and determine 810 the Recommended Basal, e.g., via using the formula Recommended Bolus=Basal*MV=1*0.7=0.7 U/hr.

Referring to FIGS. 7 and 8, after having the dose advisor output (e.g., Recommended Bolus, Recommended Basal), the user may decide whether to instruct the pump to use it or to adjust it and use a different value.

In some embodiments, when the BG is measured using a glucometer, which may require periodic evaluation of the basal rate, adjusting the basal rate according to the BG dependent IS may include periodic basal rate evaluation (e.g., every 0.5 to 4 hours). In some embodiments, when the BG level falls within the normoglycemic range during a predetermined period of time (e.g., subsequent BG measurements fall within this range), the basal rate can be re-adjusted to "normal" (i.e., to the preprogrammed value of 1 U/h in the given example).

In some embodiments, in which the BG is monitored using a CGM, then the IS, and consequently the basal rate, can be continuously adjusted (continuous may refer to frequent measurements or high rate measurements relatively to discrete measurements via a glucometer, e.g., every 3-5 minutes). The adjustment of IS value(s) and basal rate may be carried out in a closed loop mode (i.e., automatically) or in a semi-closed loop (i.e., including user's confirmation). In some embodiments, other characteristics of BG data may be used. For example, the IS dependent basal rate can be adjusted according to the average BG measured in time segments (e.g., time segments of 10-30 minutes), or according to BG trends.

In some embodiments, when the BG level is measured discretely and the basal rate is adjusted accordingly, the user may be advised to periodically check his/her BG level (e.g., every 1 hour) as a safety means or verification means to re-adjust the basal delivery rate if needed (e.g., adjusting it back to "normal" when BG level returns to normoglycemia range).

Various implementations of the dose advisor/dose advisor application described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system according to some such embodiments described above may include clients and servers. A client and server are generally remote from each other and typically interact through a communication network. The relationship of client and server arises by virtue of computer programs running on the respective computers and having a client-server relationship to each other. For example, a patient that does not have his remote control unit "at arm's length", can administer and control a bolus dose administration via the internet. Another implementation refers to a physician that is located far from the patient and device, but still able to monitor, operate and receive data from the device via the internet or a data server, e.g., a U.S. based physician can communicate with the device and patient which are situated overseas.

Preferable embodiments implement the dose advisor via software operated on or in conjunction with a processor contained in a remote control device of an insulin dispensing system and/or a processor contained in a insulin dispensing device being part of an insulin dispensing system.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any an all elements from any other disclosed methods, systems, and devices, including any and all elements corresponding to disclosed graphical-user-interfaces (GUIs). In other words, elements from one or another disclosed embodiments may be interchangeable with elements from other disclosed embodiments.

What is claimed is:

1. A method for recommending an insulin dose adapted for use with an insulin delivery device, the method comprising:

providing the insulin delivery device comprising:

a housing containing therein a pump for dispensing the insulin bolus dose into a body of a user;

input means for receiving blood glucose (BG) data;

a remote control containing therein a processor having a dose advisor application thereon configured to determine insulin sensitivity (IS) values based on corresponding BG ranges having the following IS values: BG<50→IS=170mg/dL/U, 50<=BG<70→IS=130mg/dL/U, 70<=BG<=150→IS=100mg/dL/U, 150<=BG<=200→IS=80mg/dL/U, 200<BG<=250→IS=60mg/dL/U, 250<BG<=300→IS=50mg/dL/U, and 300<BG→IS=40mg/dL/U;

a memory for storing the BG data and the IS values; and a display for presenting output associated with the IS values which comprises an IS value used for an insulin bolus dose determination and a determined insulin bolus dose;

receiving the BG data comprising a BG level;

determining one of the IS values associated with the BG data via the dose advisor application;

receiving input from the user as to an amount of carbohydrates (Carbs) the user is about to consume;

receiving, via the dose advisor application, a carbohydrate to insulin ratio (CIR), a target blood glucose level (TBG), and a residual insulin level (RI);

calculating the determined insulin bolus dose using the equation:

$$(Carbs/CIR)+(BG-TBG)/IS-RI;$$ and displaying the IS value used for the insulin bolus dose determination and the determined insulin bolus dose as the recommended insulin dose.

2. The method of claim 1, wherein the BG data further comprises a BG trend.

3. The method of claim 1, wherein receiving BG data includes at least one of: receiving an input from a user, and receiving a signal from a glucose monitor.

4. The method of claim 1, further comprising visually presenting the one or more IS values as a function of BG data.

5. The method of claim 4, wherein visually presenting includes presenting a graph or a table showing matching between the IS values and the BG data.

6. The method of claim 1, further comprising retrieving from the memory the one or more IS values associated with BG data.

* * * * *